United States Patent [19]

Bonderman

[11] Patent Number: 5,348,852
[45] Date of Patent: Sep. 20, 1994

[54] DIAGNOSTIC AND THERAPEUTIC COMPOSITIONS

[75] Inventor: Ruby P. Bonderman, Noblesville, Ind.

[73] Assignee: Analytical Control Systems Inc., Fishers, Ind.

[21] Appl. No.: 875,206

[22] Filed: Apr. 27, 1992

Related U.S. Application Data

[63] Continuation of Ser. No. 565,948, Aug. 10, 1990, abandoned.

[51] Int. Cl.$^5$ .......... C12Q 1/32; C12Q 1/42; C12Q 1/48; C12N 9/96

[52] U.S. Cl. .......... 435/4; 435/188; 436/8; 436/16; 436/18

[58] Field of Search .......... 435/188, 2, 4; 436/8, 436/12, 13, 14, 15, 16, 18

[56] References Cited

U.S. PATENT DOCUMENTS

| | | | |
|---|---|---|---|
| 1,444,250 | 2/1923 | Kern et al. | |
| 3,560,392 | 2/1971 | Eymery et al. | 252/138 |
| 4,059,967 | 11/1977 | Rowe et al. | 62/64 |
| 4,155,331 | 5/1979 | Lawrence et al. | 62/64 |
| 4,186,253 | 6/1980 | Yokoyama et al. | 435/240 |
| 4,310,625 | 1/1982 | Modrovich | 435/15 |
| 4,530,905 | 7/1985 | Freedman | 435/177 |
| 4,652,524 | 5/1987 | Modrovich et al. | 435/188 |
| 4,668,630 | 5/1987 | Louderback | 435/184 |
| 4,688,387 | 8/1987 | Conaway | 62/64 |
| 4,711,739 | 12/1987 | Kandathil | 252/139 |
| 4,923,797 | 5/1990 | Babior | |
| 4,931,361 | 6/1990 | Baldeschweiler et al. | 428/402.2 |
| 4,980,277 | 12/1990 | Junnila | 435/2 |
| 5,001,047 | 3/1991 | Liberman | 435/1 |
| 5,211,960 | 5/1993 | Babior | |

FOREIGN PATENT DOCUMENTS

| | | |
|---|---|---|
| 36573/89 | 1/1990 | Australia. |
| 623908 | 1/1990 | Australia. |
| 0346879A1 | 12/1989 | European Pat. Off. |
| 1126628 | 9/1968 | United Kingdom. |

OTHER PUBLICATIONS

W. F. Harrington and P. H. von Hippel, "The Structure of Collagen and Gelatin", *Advances in Protein Chemistry*, 16, 1961, pp. 1–138.

H. Boedtker and P. Doty, "The Native and Denatured States of Soluble Collagen", *Journal of American Chemical Society*, 78, 1956, pp. 4267–4280.

Livesey J. H., Clinica Chimica Acta 123: 193, 1982.

Kato, K., Clinica Chimica Acta 120: 261, 1980.

Kato, K., FEBS Letters 99(1):172, 1979.

De Vries, Phil. Trans. R. Soc. Lond. B 304, 575–588, 1984.

Harrison et al. "Ice growth on supercooled solutions of antifreeze glycoproteins", *Nature*, vol. 328 No. 6127 pp. 241–243 Jul. 16, 1987.

Fletcher et al. "Antifreeze peptides confer freezing resistance to fish", *Can. J. Zool.* vol. 64, 1986 pp. 1897–1901.

Knight et al. "Fish Antifreeze protein and the freezing and recrystallization of ice", *Nature* vol. 308, pp. 295–296 1984.

Pickett et al. "Sequence of Antifreeze protein precursor", *Eur. J. Biochem* 143, 35–38 1984.

Brown et al. "Direct Evidence for Antifreeze Glycoprotein Adsorption onto an Ice Surface" *Biopolymers* vol. 24, 1265–1270 1985.

Feeney "Inhibition and Promotion of Freezing: Fish Antifreeze Proteins and Ice Nucleating Proteins" *Comments Agric. & Food Chemistry* vol. 1, No. 3, pp. 147–181, 1988.

*Primary Examiner*—James C. Housel
*Assistant Examiner*—Rachel Freed
*Attorney, Agent, or Firm*—Kenyon & Kenyon

[57] ABSTRACT

Compositions, such as liquid therapeutic or diagnostic compositions, and methods for their preparation and involving their use. The compositions comprise an effective amount of gelatin from cold water fish skin as a protein base. The indicated gelatin provides many significant advantages and improvements, including for instance its high stabilizing effect on labile organic substrates included in the compositions, and its low temperature gelling properties which provide improved compositions which do not substantially gel during refrigeration. Further representative advantages relate to its behavior as a zwitterion thus reducing or eliminating needs for buffers, and its surprising behavior similar to human serum protein in protein analyses such as the biuret procedure.

12 Claims, No Drawings

DIAGNOSTIC AND THERAPEUTIC COMPOSITIONS

This application is a continuation of application Ser. No. 07/565,948, filed Aug. 10, 1990, now abandoned.

BACKGROUND OF THE INVENTION

This invention relates to improved compositions such as medical and diagnostic compositions, and to methods of their preparation and use. The improved compositions are highly stable and have desirable physical and chemical properties.

By way of further background, therapeutic, diagnostic, and other similar compositions commonly contain materials which are naturally labile (i.e. sensitive to degradation, for example by oxidation or by the action of free radicals). This is unfortunate, since the labile materials are often the active or critical component of the composition, or otherwise lead to degradation products which render the composition unsuitable for use. As will be appreciated, labile materials can be any of a large variety of substances, including for example pharmaceuticals or biologic materials such as sugars, fats, oils, hormones, enzymes, cells or cell components, blood, blood fractions, etc. Quite naturally, therefore, there has been and is a continuing interest in developing new ways to stabilize these labile materials. Further, the means used to stabilize the labile materials, in the most optimum of circumstances, would also avoid, to the greatest extent possible, interference with or complication of the procedures involved in the preparation, storage, handling and use of the compositions including them.

As one specific example, enzymes, while enjoying a wide variety of analytic and therapeutic uses, are notoriously labile. For instance, enzymes are useful in various diagnostic tests, such as the in vitro determination of creatine, blood urea nitrogen (BUN), glucose, etc. To overcome problems related to lability, enzyme preparations are often lyophilized, or the enzymes are otherwise entrained in a solid matrix imparting stability. However, this not only can escalate the cost of the final product, but also often complicates handling and use of the product. As an example, lyophilized enzyme preparations must be reconstituted with water prior to use and preferably be used shortly thereafter. Significant delay in use after reconstitution can lead to an unreliable determination. Further, it is well known that enzymes, once lyophilized and then reconstituted, frequently suffer a loss of activity. This can render determinations unreliable even if the enzymes are used immediately after reconstitution. It is therefore desirable that laboratories performing diagnostic assays have available enzyme preparations which are stable over time yet can remain in liquid form.

Accordingly, over the years, there have been attempts to prepare stabilized liquid-form enzyme compositions for use in diagnostic procedures. For example, U.S. Pat. No. 4,310,625 to Modrovich discloses a liquid enzyme preparation stabilized by an organic solvent such as propanediol. The disclosed composition comprises an aqueous medium containing a lyophilized, dry enzyme, an organic solvent such as propanediol, a very small quantity of a polymer, such as polyvinylpyrrolidine or 0.1% gelatin, and, permissibly, from 1–18% of one or more salts plus a bacteriostatic agent. As disclosed in Modrovich '625, the organic solvent protects functional group sites on the enzyme molecule. U.S. Pat. No. 4,652,524 to Modrovich delineates another method of stabilizing enzymes. According to this method, the enzyme, in a liquid medium, is reacted with a polymer having certain pendant groups capable of covalently bonding with pendant groups on the enzyme. An ethylene-maleic anhydride copolymer is one specifically described for this purpose. The process employs small amounts of gelatin (0.225% typically), albumin, dextran, a substrate and sodium azide. These ingredients are mixed in solution and the resulting solution added to the polymer solution. This new solution is then added to a solution of the enzyme in a glycerol-water medium. Alternately, the enzyme solution can be added to the first solution prior to the addition of the polymer solution.

Despite these and other attempts to provide improved stable therapeutic, diagnostic and other similar liquid compositions including labile organic substrates such as enzymes, drugs, cells, etc., the commercial situation has remained essentially the same for many years. For example, very few, if any, liquid enzyme preparations have achieved significant success in the marketplace, and reports indicating unsatisfactory stability of other therapeutic and diagnostic materials have continued. It is thus apparent that there remains a need for improved stable liquid compositions in these areas and methods for their preparation and use. The applicant's invention addresses these needs.

SUMMARY OF THE INVENTION

In certain aspects, this invention provides novel compositions such as diagnostic or therapeutic compositions and novel methods involving their preparation and use. Highlighting this invention is the applicant's discovery that gelatin derived from cold water fish skin exhibits many desirable chemical and physical properties which can be advantageously applied to these compositions and methods.

Accordingly, a first preferred embodiment of this invention relates to a liquid diagnostic or therapeutic composition including an effective amount of gelatin from cold water fish skin as a protein base.

Another preferred embodiment of this invention relates to an improved diagnostic or therapeutic method which is performed with a composition as described in the first-mentioned embodiment above.

Still another preferred embodiment relates to a method for increasing the stability of a labile organic substrate in a liquid diagnostic or therapeutic composition. This method includes the step of providing in the composition an effective amount of gelatin from cold water fish skin to increase the stability of the substrate.

Another preferred embodiment relates to a method for stabilizing a labile organic substrate in an aqueous liquid therapeutic or diagnostic composition. The method includes the step of providing in the composition an effective amount of gelatin from cold water fish skin to increase the stability of the organic substrate.

These preferred methods and compositions provide many significant improvements and advantages. For example, the applicant has discovered that gelatin from cold water fish skin is highly efficient for stabilizing labile organic substrates such as enzymes, cells, and other proteins and like substrates commonly included in diagnostic and therapeutic compositions. Further, the applicant has discovered that gelatin from cold water fish skin behaves like human serum protein in protein analyses such as the biuret procedure, and accordingly provides a superior protein base for these compositions regardless of whether they contain labile organic substrates. Moreover, this cold water fish skin gelatin has a lower gelling temperature than common gelatins derived from cows, pigs and like animals. This low-temperature gelling fish gelatin is thus ideal in applications involving liquid diagnostic, therapeutic and other similar preparations which can commonly be refrigerated prior to use. For example, the storage, handling and use of such preparations is greatly improved over that which would be encountered if conventional bovine, porcine, or similar gelatin were used—e.g. these latter gelatins, included in similar amounts, would be more apt to cause the preparation to gel during refrigeration. A gelled preparation would thereafter have to be "melted" prior to use, making the product highly unattractive.

Further, in the field of blood controls, the applicant has discovered that this gelatin from cold water fish binds to bilirubin, a major unstable component of serum controls, in such a manner that the bilirubin is highly stable if the solution is protected from light. Additionally, in the applicant's work this cold water fish skin gelatin has exhibited behavior as a zwitterion, thereby reducing or eliminating the need for added buffer in various analytical and other procedures.

As already stated, these aspects provide important advantages in improved diagnostic (e.g. controls), therapeutic, and other like compositions and methods of their preparation and use. Additional objects and advantages will be apparent upon reviewing the description which follows.

DESCRIPTION OF THE PREFERRED EMBODIMENTS

For the purposes of promoting an understanding of the principles of the invention, reference will now be made to certain embodiments and specific language will be used to describe the same. It will nevertheless be understood that no limitation of the scope of the invention is thereby intended, such alterations, and such further modifications and applications of the principles of the invention as described herein being contemplated as would normally occur to one skilled in the art to which the invention relates.

In accordance with the discussion above, one preferred embodiment of this invention relates to an improved liquid diagnostic or therapeutic composition. This improved composition includes an effective amount of gelatin from cold water fish skin to provide a beneficial protein base. In one aspect, the gelatin from cold water fish provides a beneficial protein base for the composition regardless of whether it contains a labile organic substrate. In another aspect, the composition can comprise an organic substrate sensitive to degradation therein (e.g. an enzyme, pharmaceutical, cell, blood fraction, hormone, etc.), and the gelatin from cold water fish skin is further included in an effective amount to increase the stability of the organic substrate.

As will be understood, the labile organic substrate can be any one of many types well known and often used in diagnostic, therapeutic and other similar disciplines. For example, representative labile substrates include biological materials such as enzymes, cells and their components, hormones, blood proteins, etc., as well as pharmaceuticals and drugs including preparations of naturally-occurring materials and/or synthetic materials. As typical enzymes, there may be mentioned glutamic-oxaloacetate transaminase, glutamic-pyruvate transaminase, lactic dehydrogenase, creatine phosphokinase, acid phosphatases, amylases, alkaline phosphatases, glutamyl transpeptidases, isocitric dehydrogenase, alpha-hydroxybutyric dehydrogenase, lipase, alanine amino transferase, esterases, aspartate amino transferase, malic dehydrogenase, glucose-6-phosphate dehydrogenase, peroxidase, cholesterol oxidase, cholesterol esterase, uricase, urease, glycerol kinase and the like. Representative cells included in the applicant's work thus far have been red and white blood cells. Typical therapeutic substrates can include pharmaceuticals, enzymes, hormones, etc. having therapeutic value, including for example substances such as tissue plasminogen activator, insulin, human growth hormone, etc. In general, these and other similar substrates have proven to be relatively labile (i.e. sensitive to degradation, as by oxidation or the action of free radicals), especially in aqueous or partly aqueous mediums often encountered in therapeutic or diagnostic compositions. Particularly preferred substrates based on work to date are enzymes such as creative phosphoslainase (CPK) and lactate dehydrogenase (LDH), as well as uric acid, blood urea nitrogen (BUN), glucose, cholesterol, triglycerides, bilirubin, and red and white blood cells. Further, in one preferred mode of carrying out the invention, the applicant's discoveries provide dramatic improvements to serum controls. When such a control is shielded from light, the cold water fish gelatin highly stabilizes bilirubin, which has been particularly troublesome and long recognized as a major unstable component of serum controls.

The amount of any organic substrate included will, of course, depend upon the particular diagnostic or therapeutic chemistries or applications involved. However, for purposes of illustration, liquid enzyme preparations in accordance with the invention will typically include about 1 units/l to about 50,000 u/l of enzyme. Further, in many therapeutic and diagnostic compositions, the substrate of interest is included in purified form (e.g. in the case of purified enzymes and other concentrates), most often preferably at least about 90% pure. As will be appreciated by those practiced in these fields, however, specific concentrations or amounts of organic substrates in the compositions can vary widely within the scope of the present invention.

As stated above, the gelatin included in the composition is gelatin from cold water fish skin, which has demonstrated a gelling temperature substantially lower than that of typical land animals such as cows or pigs. As an example, a 10% aqueous solution of the preferred cold water fish skin gelatin (teleostean) commercially available from Sigma Chemical Company, St. Louis, Mo., U.S.A., (product number G 7765) gells only partially even at a low temperature of about 0°–2°, whereas a similar 10% solution of porcine gelatin gells at a temperature of about 25°–28°. The gelatin from cold water fish skin is included in an effective amount to provide a protein base for the composition. It is further preferred that the effective amount thus included nevertheless not cause substantial gelling of the composition during refrigeration at a temperature of about 10° C., preferably as low as about 5° C. Preferably, this gelatin is included in an amount of about 0.5 to about 10 wt. % relative to the weight of the composition, and more preferably about 6 wt. %. Further, the pH of the composition can be adjusted with a suitable acid, to obtain a final pH suitable for the substrate. For example, most enzymes can be maintained at a pH between about 6 and 8, more preferably about pH 6.5. Any suitable acid for such pH adjustment as known in the art can be used; however, preferred to date in the applicant's work has been lactic acid. Further, suitable antibacterials such as sulfamethoxazol, trimethoprim, gentamycin sulfate, ampicillin, or other known systems compatible with the substrate can be included in the composition. As other examples, in the case of glucose, cholesterol, triglycerides, and many soluble analytes, the composition preferably contains additional additives such as sodium benzoate (preferably about 1%), EDTA (preferably about 1%), and glycine buffer.

As indicated above, additional of the applicant's discoveries make it desirable to include an effective protein base including gelatin from cold water fish skin, regardless of whether the composition contains a labile organic substrate. For example, the gelatin has proven to act as a zwitterion, thus reducing or eliminating the need for added buffer in the composition. Further, the low-temperature gelling properties of this gelatin make it desirable for diagnostic controls or therapeutic compositions which are used as liquids and are commonly refrigerated—i.e. more gelatin from cold water fish can be included in the composition as compared to cow, porcine or like gelatin, without leading to a product which gels during refrigeration. Accordingly, this gelatin can provide a highly effective protein base for diagnostic controls or like compositions containing substrates such as electrolytes, bicarbonate, calcium, magnesium, etc., whereby these substrates as they occur in natural biological fluids or other similar unknowns can be effectively assayed. When these preferred substrates are included, the composition also preferably contains sodium azide or another appropriate antibacterial, and the pH of the composition is most preferably maintained at about pH 8 to 8.5, more preferably about 8.2. Further, these antibacterial/pH conditions have also proven to be preferred for stabilizing compositions containing bilirubin.

Still other preferred embodiments of the invention relate to methods for preparing stable liquid diagnostic or therapeutic compositions, and to therapeutic and diagnostic methods including the use of compositions described herein. These methods incorporate the principles and parameters set forth in the description above and further illustrated in the specific Examples which follow.

For the purposes of promoting a further understanding of invention and its advantages, the following Examples are provided. Unless otherwise specified, percents given are percents by weight. Additionally, none of the compositions prepared as described below exhibits any substantial gelling during refrigeration at about 10° C.

EXAMPLE 1

Stable Liquid Glucose Compositions 14 grams of gelatin from cold water fish skin available from Sigma Chemical Company, Product No. G 7765 (a 45% aqueous solution containing 0.15% propyl p-hydroxybenzoate and 0.20% methyl p-hydroxybenzoate as preservatives) are added to a volumetric flask, and diluted to 100 ml with distilled water. Sufficient glucose is then added to achieve a value (frozen) of 66 mg/dl in the composition. Sodium benzoate and EDTA are added, both to a final concentration of about 1%.

Glycine buffer is added to a final concentration of about 0.7%. An identical preparation is also performed, except sufficient glucose is added to achieve a value (frozen) of 138 mg/dl in the composition. Samples of the compositions thus formed are subjected to various time/temperature stability analyses. The results are given in Table 1.

TABLE 1

| Temperature | Time | VALUE | |
|---|---|---|---|
| | | 66 mg/dl | 138 mg/dl |
| 37° C. | 3 weeks | 65 | 138 |
| 37° C. | 4 weeks | 66 | 137 |
| 37° C. | 5 weeks | 65 | 139 |
| 25° C. | 2 months | 64 | 139 |
| 25° C. | 3 months | 65 | 140 |

EXAMPLE 2

Stable Liquid Glucose Compositions

Example 1 is repeated, except three stable compositions are prepared having respective glucose values (frozen) of 99, 101, and 98 mg/dl. Samples of each of these compositions are maintained for two weeks at the temperatures given in Table 2 below. As the results show, each composition has excellent stability over a wide temperature range. From the data of Examples 1 and 2, it is apparent that no Amodori reaction occurs between the glucose and the gelatin and hence no glycation. This means a reliable glucose value can be recovered when the product is analyzed.

TABLE 2

| Temperature | VALUE | | |
|---|---|---|---|
| | 99 mg/dl | 101 mg/dl | 98 mg/dl |
| 37° C. | 98 | 104 | 96 |
| 25-28° C. | 98 | 101 | 97 |
| 0-8° C. | 100 | 101 | 98 |

EXAMPLE 3

Stable Liquid Cholesterol Compositions

Example 1 is repeated, except animal lipoprotein containing cholesterol is added instead of the glucose, to final cholesterol values (frozen) of 200, 182, and 164 mg/dl in respective compositions. Samples of each lipoprotein protein cholesterol composition are maintained for two weeks at the temperatures given in Table 3 below, and then retested. Again, the results show excellent stability.

TABLE 3

| Temperature | VALUE | | |
|---|---|---|---|
| | 200 mg/dl | 182 mg/dl | 164 mg/dl |
| 37° C. | 196 | 176 | 161 |
| 25-28° C. | 198 | 181 | 163 |
| 0-8° C. | 202 | 181 | 164 |

EXAMPLE 4

Stable Liquid Uric Acid Compositions

Example 1 is repeated except uric acid is added instead of the glucose, to achieve final uric acid values (frozen) of 5, 5, and 10 mg/dl in three respective compositions. Samples of each composition are maintained for two weeks at the temperatures set forth in Table 4 below, and then retested. As can be seen, good stability is achieved.

TABLE 4

| Temperature | VALUE | | |
|---|---|---|---|
| | 5 mg/dl | 5 mg/dl | 10 mg/dl |
| 37° C. | 6 | 4 | 7 |
| 25-28° C. | 6 | 4 | 8 |
| 0-8° C. | 5 | 5 | 8 |

EXAMPLE 5

Stable Liquid Blood Urea Nitrogen (BUN) Compositions

Example 1 is repeated, except BUN is added instead of the glucose, to achieve final values (frozen) of 4.3, 4.4, and 4.3 in three respective liquid compositions. Samples of the three compositions are maintained for two weeks at the temperatures indicated in Table 5 below, and then retested. Excellent stability is again demonstrated.

TABLE 5

| Temperature | VALUE | | |
|---|---|---|---|
| | 4.3 mg/dl | 4.4 mg/dl | 4.3 mg/dl |
| 37° C. | 4.6 | 4.5 | 4.5 |
| 25-28° C. | 4.3 | 4.4 | 4.4 |
| 0-8° C. | 4.4 | 4.3 | 4.3 |

EXAMPLE 6

Stable Red and White Blood Cell Compositions

Example 1 is repeated, except red and white blood cells are added to respective compositions instead of the glucose. The compositions are then maintained at 37° C. for three weeks. Upon staining with Wrights stain and microscopic examination, it is found that no significant degradation of the red or white blood cells has occurred, proving the excellent stabilizing effect of the cold water fish gelatin on these substrates.

EXAMPLE 7

Stable Liquid Triglyceride Compositions

Example 1 is repeated, except triglycerides obtained from hen's egg yolk and from animal serum lipoprotein are added instead of the glucose. Similar time/temperature stability tests demonstrate that the triglyceride containing formulations are stabilized in the compositions.

EXAMPLE 8

Stable Liquid Bilirubin-Containing Compositions 14 g of the gelatin from cold water fish skins as in Example 1 are diluted to 100 ml with distilled water. Bilirubin is then added to a value of 22 mg/dl. Sodium azide is added in an amount of about 0.1% as an antibacterial. The pH of the composition is maintained at about 8.2 with glycine buffer. The composition is maintained in a dark environment for 2 weeks at a temperature of 37° C. Thereafter, routine analysis indicates no significant loss of the bilirubin value. Following these results, about 0.5-2% by weight of the cold water fish gelatin is added to a buffered human serum control preparation (also containing sodium azide). It is found that bilirubin in the control is thereby stabilized, and the control performs admirably in conventional serum assays.

EXAMPLES 9-11

Bicarbonate, Magnesium and Calcium Compositions

The initial preparation of Example 1 is repeated, except in respective compositions, calcium, magnesium, and bicarbonate, are added instead of the Glucose. The resulting compositions are stable, and the presence of the cold water fish gelatin provides a protein base which renders the compositions excellently suited during use as controls.

EXAMPLE 12

Stable Liquid Lactate Dehydrogenase (LDH) Composition 14 grams of gelatin from cold water fish skin as in Example 1 are added to a volumetric flask, and diluted to 100 ml with distilled water and 10 to 500 u of LDH concentrate. Sulfamethorazol is added in an amount of about 0.1 wt. % as an antibacterial agent. The pH of the mixture is adjusted to 6.5 with lactic acid. The resulting liquid LDH enzyme preparation has good storage stability at both room temperature and during refrigeration at about 0°-8° C.

EXAMPLE 13

Stable Liquid Creatine Phosphokinase (CPK) Composition

Example 12 is repeated, except CPK concentrate from human and animal source is used instead of the LDH concentrate. The resulting liquid CPK composition demonstrates good storage stability at room temperature and during refrigeration at about 0°-8° C.

While the invention has been illustrated and described in detail in the foregoing description, the same is to be considered as illustrative and not restrictive in character, it being understood that only the preferred embodiment has been described and that all changes and modifications that come within the spirit of the invention are desired to be protected.

I claim:

1. A liquid diagnostic control composition suitable for reproducibly monitoring the concentration of an enzyme in a biological fluid from a patient wherein said enzyme has a predetermined stability in said fluid, said diagnostic composition comprising between about 0.5 and about 10% on a per weight basis of gelatin from a cold water fish and an amount of said enzyme, said enzyme being of greater stability in said control than in said fluid and wherein said composition is substantially ungelled at a temperature of about 10° C.

2. A diagnostic control composition according to claim 1, wherein said enzyme is creatine phosphokinase.

3. A diagnostic control composition according to claim 1, wherein said enzyme is lactate dehydrogenase.

4. A diagnostic control composition according to claim 1 wherein said enzyme is glutamyl transpeptidase.

5. A diagnostic control composition according to claim 1 wherein said enzyme is aspartate aminotransferase.

6. A diagnostic control composition according to claim 1 wherein said enzyme is alkaline phosphatase.

7. A diagnostic blood control composition according to claim 1, wherein said gelatin is present in a concentration of about 6%.

8. A diagnostic control composition according to claim 1 wherein said enzyme is selected from the group consisting of lactate dehydrogenase, creatine phosphokinase, aspartate aminotransferase, alkaline phosphatase, malic dehydrogenase, glucose-6-phosphate dehydrogenase, esterase, glutamic-oxaloacetate transaminase, glutamic-pyruvate transaminase, acid phosphatase, amylase, glutamyl transpeptidase, isocitric dehydrogenase, alpha-hydroxybutyric dehydrogenase, lipase, alanine aminotransferase, peroxidase, cholesterol oxidase, cholesterol esterase, uricase, urease and glycerol kinase.

9. A diagnostic control composition according to claim 1 wherein said enzyme is a blood constituent.

10. A liquid diagnostic control composition comprising between about 0.5 and about 10% on a per weight basis of gelatin from a cold water fish and an enzyme and wherein said composition is substantially ungelled at a temperature of about 10° C.

11. A liquid diagnostic control composition suitable for reproducibly monitoring the concentration of an enzyme in a biological fluid from a patient, said diagnostic composition comprising between about 0.5 and about 10% on a per weight basis of gelatin from a cold water fish and an enzyme selected from the group consisting of creatine phosphokinase, lactate dehydrogenase, glutamyl transpeptidase, aspartate aminotransferase and alkaline phosphatase and wherein said composition is substantially ungelled at a temperature of about 10° C.

12. A liquid diagnostic control composition suitable for reproducibly monitoring the concentration of an enzyme in a biological fluid from a patient, said diagnostic composition comprising between about 0.5 and about 10% on a per weight basis of gelatin from a cold water fish and an enzyme selected from the group consisting of lactate dehydrogenase, creatine phosphokinase, aspartate aminotransferase, alkaline phosphatase, malic dehydrogenase, glucose-6-phosphate dehydrogenase, esterase, glutamic-oxaloacetate transaminase, glutamic-pyruvate transaminase, acid phosphatase, amylase, glutamyl transpeptidase, isocitric dehydrogenase, alpha-hydroxybutyric dehydrogenase, lipase, alanine aminotransferase, peroxidase, cholesterol oxidase, cholesterol esterase, uricase, urease and glycerol kinase and wherein said composition is substantially ungelled at a temperature of about 10° C.

* * * * *